United States Patent [19]

Williams

[11] 4,332,122
[45] Jun. 1, 1982

[54] METHOD OF MAKING AND FILLING LIQUID-CONTAINING STERILE PACKAGES SUCH AS BLOOD BAGS

[75] Inventor: Ronald A. Williams, Mundelein, Ill.

[73] Assignee: Baxter Travenol Laboratories, Inc., Deerfield, Ill.

[21] Appl. No.: 161,975

[22] Filed: Jun. 23, 1980

Related U.S. Application Data

[62] Division of Ser. No. 927,342, Jul. 24, 1978, Pat. No. 4,223,675.

[51] Int. Cl.³ ............................................. B65B 55/02
[52] U.S. Cl. ................................. 53/425; 128/214 D; 128/272; 53/127
[58] Field of Search ..................... 53/425, 426, 127; 128/272, 214.2, 214 R, 214 D

[56] References Cited

U.S. PATENT DOCUMENTS

| | | | |
|---|---|---|---|
| 2,702,034 | 2/1955 | Walter | 128/272 X |
| 2,838,046 | 6/1958 | Butler | 128/272 |
| 3,064,647 | 11/1962 | Earl | 128/272 X |
| 3,177,870 | 4/1965 | Salem, Jr. et al. | 128/272 X |
| 3,187,750 | 6/1965 | Tenczar, Jr. | 128/272 |
| 3,467,095 | 9/1969 | Ross | 128/214.2 |
| 3,809,845 | 5/1974 | Stenstrom | 53/425 |
| 3,945,380 | 3/1976 | Dabney et al. | 128/214 R |
| 4,065,816 | 1/1978 | Sawyer | 53/425 X |
| 4,177,620 | 12/1979 | Daly et al. | 53/425 |

*Primary Examiner*—James F. Coan
*Attorney, Agent, or Firm*—Paul C. Flattery; Raymond Mehler; Daniel D. Ryan

[57] ABSTRACT

Packages or containers are formed for body fluids or other solutions within which autoclaved liquids such as anticoagulants are included. The invention, which is particularly suitable for donor blood bags, includes the use of a sterile connector to incorporate autoclaved liquids into sterilized packages that can, if desired, be made of materials that cannot be successfully autoclaved at high temperatures without deformation or discoloration thereof.

11 Claims, 6 Drawing Figures

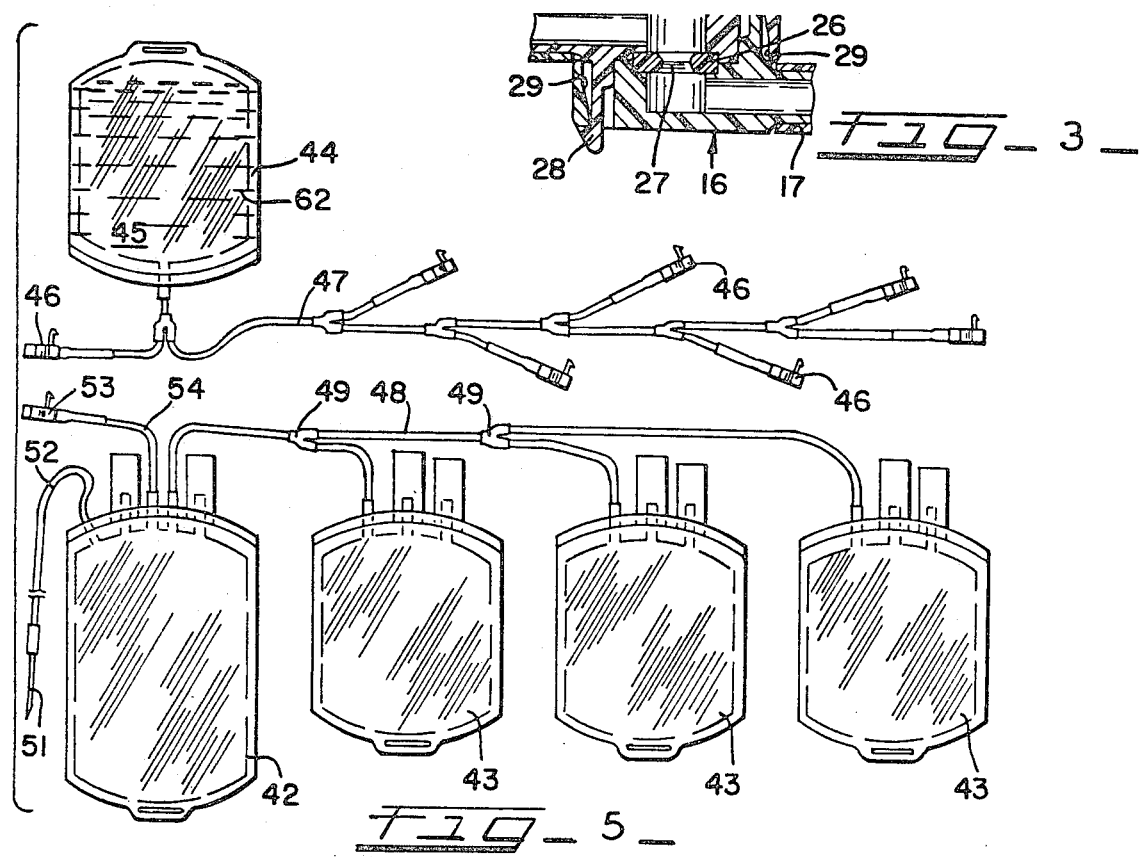
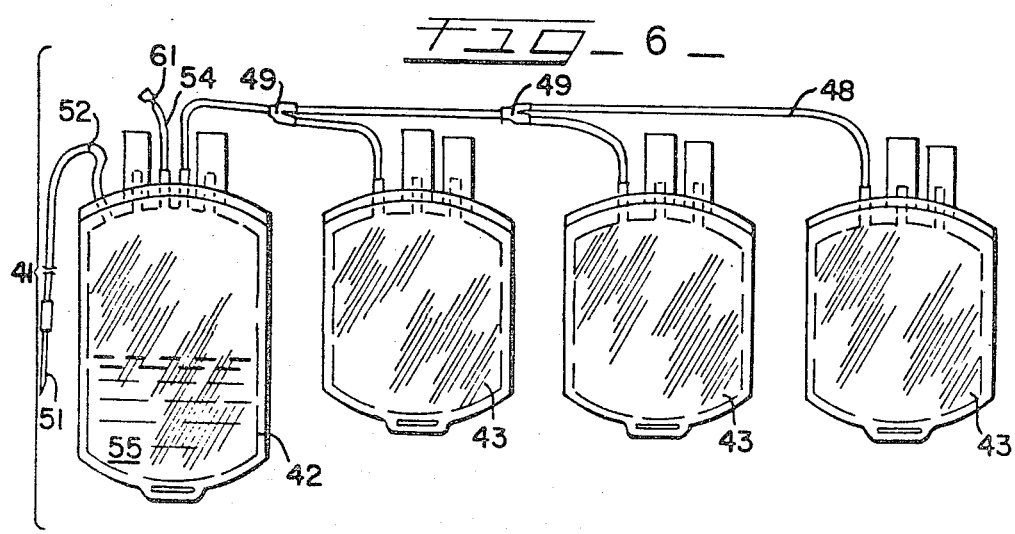

METHOD OF MAKING AND FILLING LIQUID-CONTAINING STERILE PACKAGES SUCH AS BLOOD BAGS

This is a division of application Ser. No. 927,342, filed July 24, 1978, now U.S. Pat. No. 4,223,675.

BACKGROUND AND DESCRIPTION OF THE INVENTION

The present invention relates generally to sterile containers for solutions, being particularly suitable for blood packs within which an autoclaved liquid is stored. This invention encompasses a method and a system or apparatus for preparing sterile containers such as blood bags out of either autoclavable or non-autoclavable materials, as well as the containers made thereby, which containers may be formed of materials that can exhibit superior properties other than those associated with the ability to resist damage under autoclave conditions.

Autoclaved body fluid containers having liquids autoclaved in situ therewithin are well known in the medical equipment art. Representative of this type of flexible packaging are the structures known in Earl U.S. Pat. No. 3,064,647, which specifies that the blood packs described therein are fabricated of plastics such as polyvinyl resins that are able to withstand autoclave conditions, generally understood to include heating in steam and/or hot water baths at a temperature of about 114° C. or more for from about 30 minutes to about one hour. When in use within blood donor systems, this packaging is supplied with a sterile liquid therewithin, usually an anticoagulant. Having a liquid that must be sterile within the package has heretofore dictated the sterilization thereof by a wet sterilization technique compatable with having liquids within the item being sterilized, typically an autoclave process.

Preparing sterile packaging with sterile liquids therewithin heretofore has been carried out by introducing unsterilized liquid into a portion of the container, which liquid will be sterilized together with the container itself, including portions thereof that do not contain the liquid, during subsequent wet sterilization operations carried out within an autoclave apparatus. In such systems it is critical that the material out of which the blood bag or the like is molded will not be damaged, melted, deformed or discolored during the autoclave operation, requiring a plastic having a relatively high melting point, having a relatively high deformation temperature, and otherwise being able to withstand deterioration under autoclave conditions. Even a material such as polyvinyl chloride, in wide use today for such autoclavable packaging, is not entirely satisfactory in this regard because it does tend to exhibit some undesirable changes and can be damaged at optimal autoclave temperatures of 120° C. or higher, often making it necessary to use slightly less than optimum, but still sterilization effective, autoclave temperatures.

Providing blood bags and the like fabricated out of autoclavable materials such as polyvinyl chloride has other potentially undesirable ramifications. Residual plasticizers within certain polymers such as polyvinyl chloride tend to be leached out when blood is stored within such materials for extended time periods. In addition, polyvinyl chloride may not afford optimum storage parameters and does not exhibit the extent of gas permeability that is highly desired for blood packaging.

Certain materials, heretofore unacceptable because of their non-autoclavable properties, are potentially more suitable than autoclavable resins for use as materials for blood bags and the like because they exhibit overall storage parameters superior to those of presently used autoclavable materials such as polyvinyl chloride. Potential leaching problems could also be minimized, if not obviated, by eliminating the need for autoclaving the plastic material itself to significantly reduce the susceptibility of extractables such as residual plasticizers to leach out, which is brought about by subjecting the material to the stress conditions of autoclave operations. Such non-autoclavable materials can also exhibit improved gas permeability properties known to be superior for platelet storage. Certain non-autoclavable materials exhibit increased gas permeability in order to bring about optimum pH adjustments by the passage of gases, especially oxygen and carbon dioxide, through the walls of blood bags made therefrom.

By the present invention, it is possible to use these non-autoclavable materials having such advantageous properties for forming blood bags and the like which must be sterile and which must have a sterile liquid such as an anticoagulant stored therewithin. In an important aspect of this invention, it is possible for the first time to utilize sterilization techniques which heretofore could be put into practice only for preparing sterile products that are essentially completely dry; these dry systems, which are conducted at temperatures significantly lower than autoclave temperatures, include gas sterilization systems and radiation sterilization techniques. In this regard, gas sterilization systems cannot be used to sterilize liquids, and were one to attempt to substitute radiation sterilization techniques for the autoclave techniques used in preparing blood bags having a liquid anticoagulant therein, an undesirable generation of free radicals would result.

These various aspects and advantages of this invention are brought about by a system wherein liquid-containing blood bags or the like, which can be fabricated of non-autoclavable materials such as those mentioned generally for use within dry systems in Walter U.S. Pat. No. 2,702,034, and which can be subjected to dry sterilization conditions to avoid the disadvantages brought about by autoclaving and by using autoclavable materials. Liquid anticoagulant or the like is separately sterilized, typically under autoclave conditions, either in bulk or in premeasured, disposible containers or dispensers. Sterile connector means of the type disclosed in copending Granzow et al., U.S. Ser. No. 843,608, filed in October, 1977, depend from the blood bag or other package and from the dispenser containers to permit sterile transfer of the autoclaved liquid into the previously sterilized unit in order to provide a finished sterile product having autoclaved liquid therewithin, but which finished product itself need not have been subjected to autoclaved conditions.

It is accordingly a general object of the present invention to provide a sterile container that need not have been autoclaved.

Another object of the present invention is an improved system, process, and product produced thereby resulting in a sterile container for body fluids that includes an autoclaved liquid therewithin but which need not itself have been autoclaved.

Another object of this invention is an improved system, process, and product utilizing molding resins that cannot be autoclaved but which may exhibit properties desirable for the storage of body fluids that may not be typically exhibited by autoclavable plastic resins.

Another object of the present invention is an improved system, process, and product which incorporate dry sterilization techniques in conjunction with sterile connectors for sterile transfer of autoclaved liquids into a dry-sterilized container.

These and other objects of the present invention will be apparent from the following detailed description, taken in conjunction with the drawings in which:

FIG. 3 is an enlarged, sectional view of the joined sterile connection means of FIG. 2;

FIG. 5 is an elevational view showing an alternative embodiment including multiple-unit autoclavable dispenser having multiple sterile connecting means in combination with a solution containing package having four containers; and FIG. 6 is an elevational view of the finished product made in accordance with the embodiment of FIG. 5.

Figure 1:
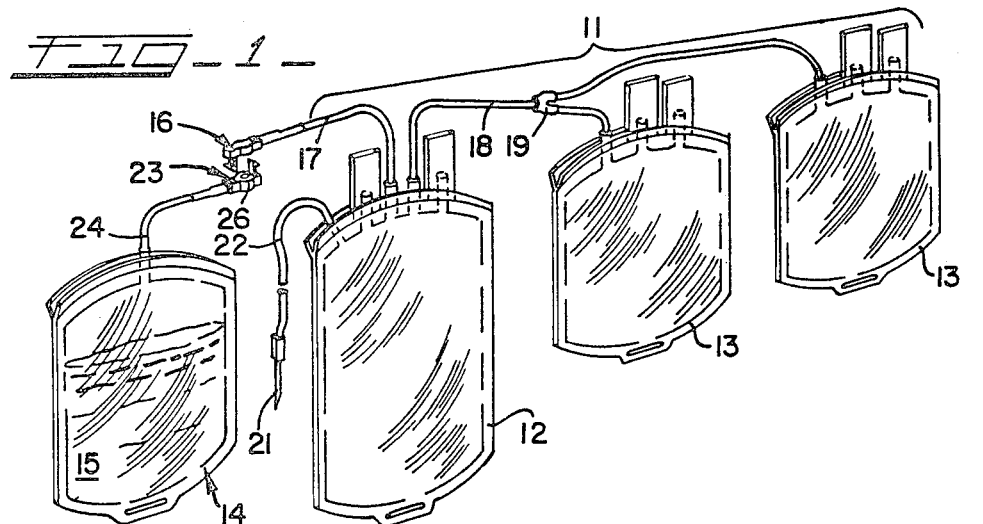
FIG. 1 is a perspective view of the system in accordance with the present invention showing, detached from each other, both a preferred form of unit autoclavable dispenser and a preferred form of solution containing package, having three containers.

FIG. 1 shows an embodiment of a solution container or package generally indicated at 11. The particular embodiment shown is that of a blood bag having a primary blood receiving container 12 and two secondary containers 13, all of which may be fabricated out of a non-autoclavable material. Also shown is a unit sterilizable dispenser, generally designated as 14, for enclosing liquid 15 therein during combined sterilization of the dispenser 14 and the liquid 15. A subsequent sterile transfer moves the sterilized liquid into the primary container 12 of the non-autoclaved packaging unit 11.

More particularly, the solution container or package 11, prior to transfer of the liquid 15 thereinto, includes a sterile connector 16, communicating through plastic tubing 17 with the primary container 12. The primary container 12 and the secondary container 13 are joined by a suitable tether and transfer tubing network 18 including a Y-joint 19. Also included is a disposable needle 21 and its associated tubing 22 opening into the primary container 12. Another sterile connector 23 is in liquid passing communication with the sterilizable dispenser 14 through suitable tubing 24.

Figure 2:
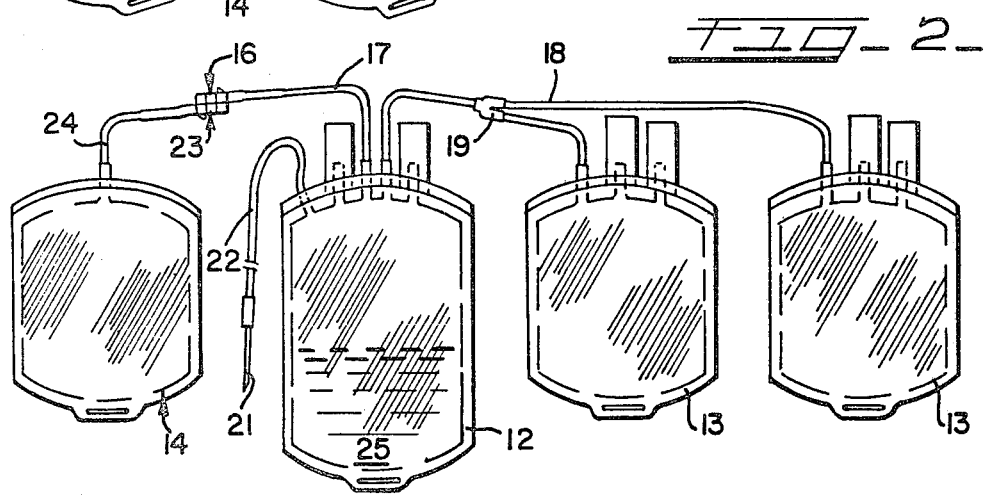
FIG. 2 is an elevational view of the embodiment shown in FIG. 1, joined at the sterile connection means.

FIG. 2 shows the sterile connectors 16 and 23 after they have been joined and brought into sterile communication with each other, followed by expressing or otherwise transferring the liquid at 15 within the sterilizable dispenser 14 through the tubing 24, the sterile connectors 23, 16, the plastic tubing 17, and into the primary container 12, at which time it may be an autoclaved liquid 25 within a non-autoclaved primary container 12. Specific features of the preferred sterile connectors 16 and 23 are depicted in FIG. 3 and are explained in full detail within said co-pending Granzow et al., U.S. Ser. No. 843,608, which is incorporated by reference herein. Basically, each sterile connector includes an opaque, thermoplastic wall portion 26 (FIG. 1) which is preferably carried within a transparent wall portion of each sterile connector 16 and 23. The opaque wall portions of the connectors are brought together into facing contact (FIG. 2) and then exposed to sufficient radiant energy to cause the opaque wall portions 26 to generally fuse together and open a sterile aperture 27 through the fused opaque wall portions 26 for providing a sterile, sealed means of communication between the autoclavable dispenser 14 and the primary container 12. The security of this communication is enhanced by providing bayonets 28 for mating operative interengagement with opposed slots 29 in the respective sterile connectors 16 and 23.

Figure 4:
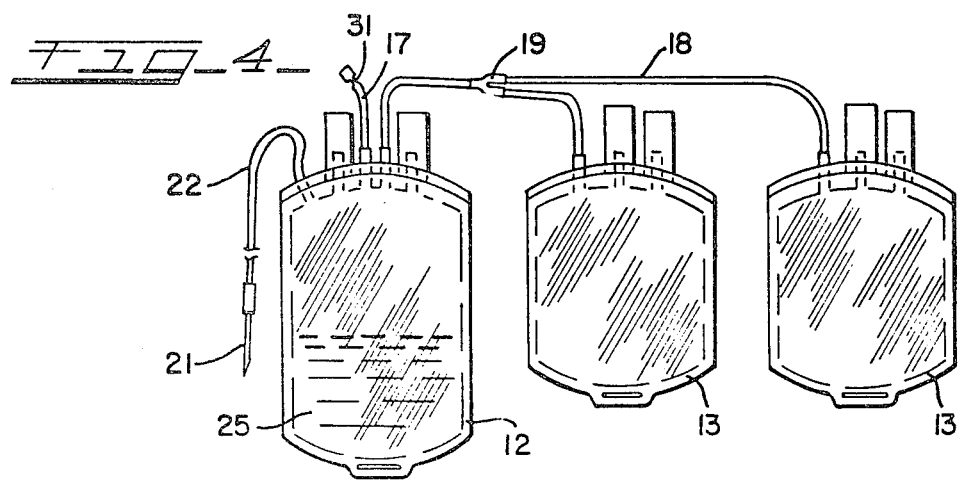
FIG. 4 is an elevational view of the embodiment shown in FIGS. 1 and 2, depicted after transfer of autoclaved liquid into the packaging unit and the subsequent removal of the sterile connecting means.

After the liquid 15 passes through the aperture 27 and into the primary container 12 as the sterilized liquid 25, the plastic tubing 17 is permanently sealed by conventional means such as a tubing heat or radio frequency sealing apparatus (not shown) in order to form a seal 31 (FIG. 4) between the sterile connector 16 and the primary container 12. Thereafter, the plastic tubing 17 is severed at a location between the sterile connector 16 and the heat seal 31 in order to form the finished packaging unit, which need not be autoclaved, having liquid 25 which may be autoclaved, as depicted in FIG. 4. This finished product is suitable for use in collecting blood from a donor by means of the disposable needle 21, the whole blood being collected within the primary container 12 at which time it will mix with the sterilized liquid 25 to bring about the desired effect, usually that of retarding coagulation of the collected whole blood. Secondary containers 13 can be used in accordance with conventional practices for the purpose of separating the whole blood into desired constituent parts.

FIGS. 5 and 6 illustrate an alternative embodiment, an important aspect of which is that it is associated with a multiple unit sterilizable dispenser 44 that is capable of introducing liquid 45 into a plurality of primary containers 42 of solution container packaging units generally referred to by 41. The multiple-unit sterilizable dispenser 44 has a network 47 of sterile connectors 46 depending therefrom, the network 47 including appropriate tubing and joints. When desired to transfer a unitary portion of the liquid 45 within dispenser 44, one of the sterile connectors 46 is operatively interconnected to sterile connector 53 in communication with the primary container 42 through tubing 54, after which a unitary portion of the liquid 45 is passed, by pumping, expressing, or the like into primary container 42 which may be as autoclaved liquid 55. A plurality of graduated markings 62 may be provided for measuring the unitary portions of liquid 45.

After the unitary portion of liquid 45 has been passed into primary container 42, typically as autoclaved liquid 55, the tubing 54 is permanently sealed at 61, followed by severing the tubing 54 at a location between sterile connector 53 and the seal 61.

In using either non-autoclaved package 11, 41, as a blood bag, whole blood is drawn from a donor through disposable needle 21, 51 and its associated tubing 22, 52, into the primary container 12, 42, and into contact with the autoclaved liquid 25, 55. Tubing 22, 52 is then sealed and the disposable needle 21, 51 is removed. If whole blood is to be broken down into its constituent parts, such parts may be divided out by centrifugation, freezing or other suitable means and transported into the secondary containers 13, 43 through the tether and transfer tubing network 18, 48 having Y-joints 19, 49.

The method of this invention relates generally to providing containers made of either non-autoclavable or autoclavable materials that have sterilized liquids stored therewithin. A liquid is sterilized in a dispenser container by conventional sterilization techniques such as by autoclaving at elevated temperatures for extended periods of time. Packaging made of either non-autoclavable or autoclavable materials is sterilized by a sterilization technique suitable for that material. Thereafter, the sterilized liquid and the sterilized package are connected in a sterile manner to each other, and the sterilized liquid is transferred into the sterilized package which is then suitably sealed in order to form the desired finish product.

More particularly, the step of sterilizing the liquid within the dispenser container will typically be accomplished by autoclave techniques including heating the liquid sealed within its autoclavable container or dispenser within a steam and/or hot water bath at a temperature of about 114° C. or more for from about 30 minutes to about one hour. Appropriate autoclavable containers include those constructed of heat-resistant glass and high melting point resins such as the polyvinyl resins, most typically polyvinyl chloride. The liquid is one of those required to be contained in a sterile condition within the particular final product being made, for example being a liquid anticoagulant for incorporation within a sterile blood bag for use in blood donor programs.

In the preferred packaging sterilizing steps of this invention, a packaging unit made of non-autoclavable materials is dry sterilized by conventional techniques such as by gas sterilization procedures or by radiation sterilization operations. Non-autoclavable materials are, in general, synthetic resins that are less heat resistant than autoclavable materials or materials that exhibit heavy discoloration or water blush retention during autoclave operations. Examples include ethylene vinyl acetate polymers and blends thereof. Other examples include ethylene vinyl acetate polymers and blends thereof. Other examples include low density polyethylene blends, blends including styrene-butiadiene block copolymers such as Kraton G (Trademark of Shell Oil Company) which exhibit marginal autoclavability, as well as other polymers, copolymers and blends which exhibit a significant water blush problem when autoclaved and/or which exhibit only marginal autoclavability. When the packaging unit is made of autoclavable materials such as polyvinyl chloride, they may be sterilized under autoclave, wet-sterilization, or other conditions suitable for such materials.

With more particular reference to the preferred dry-sterilization techniques themselves, these can be exemplified by two general classes, radiation sterilization, and gas sterilization. In radiation sterilization, the materials to be treated are subjected to gama rays or electron beams at between about 1 megarad to about 5 megarads, using standard dosages and conventional equipment. Gas sterilization techniques can take on various particular applications, such as that shown in McDonald U.S. Pat. No. 3,068,064, incorporated by reference herein. A preferred sterilizing gas is ethylene oxide. Ethylene oxide gas sterilization cycles can be generally broken down into three distinct operations: preconditioning, exposure, and post-evacuation or flushing. Such processes often include raising the temperature of the material being sterilized to a limited extent in order to maintain the most desirable properties of the sterilizing gas, the typical temperature range being between about 20° to about 70° C.

By proceeding with the wet-sterilization of only the liquid and its temporary container or dispenser, it is possible to raise the liquid to temperatures higher than those presently employed. Under present practices, it is necessary to autoclave blood bags at relatively low autoclave temperatures to avoid minor damage to or discoloration of the finished bags. In the present process, these problems are obviated either because the temporary container or dispenser is discarded after the autoclaved liquid is transferred therefrom, which eliminates the need to hold the temperature down to avoid minor container damage such as the onset of water blush conditions, or because the temporary container or dispenser is made of heat-resistant glass or the like which can be autoclaved several times without damage. By the process of this invention, the sterilized liquid can be raised to temperatures above 120° C., whereas in current commercial operations, it is difficult to safely raise the temperature above 114° C.

Having completed both the liquid sterilization and the packaging sterilization steps, the sterile connecting step is next accomplished in order to provide a secure and sterile flow path between the sterilized liquid and the sterilized packaging unit. The preferred sterile connecting steps include providing an opaque thermoplastic material embedded within each of two sealed conduits in sterile communication with the sterilized liquid and with the sterilized packaging unit, respectively. These opaque wall portions are brought together into opposed, facing contact, and the respective conduits are securely fastened to each other in the vicinity of the opaque wall portions, after which the opaque wall portions are exposed to radiant energy of a type and magnitude in order to fuse them together while opening an aperture therethrough and while simultaneously sterilizing the thus fused wall portions and the sealed conduits surrounding them in order to provide a sterile passageway connecting the respective sealed conduits.

Applying the radiant energy as described will not significantly affect the physical appearance or characteristics of any of the materials other than the opaque thermoplastic wall portions which are specifically designed to be responsive to the radiation in order to achieve the desired results. For example, it is preferred that the immediate environment of the opaque wall portions be transparent to permit the radiant energy to pass therethrough and be made of a material which is not significantly softened under the specific radiant energy conditions used in the process. Typically, the melting temperature developed at the thermoplastic opaque wall portions will be on the order to 200° to 250° C. Radiant energy sources can include visible, infrared, ultraviolet, radio frequency, or laser energy.

Once the sterile connecting step is completed, a predetermined quantity or unit of the sterilized liquid is transported under sterile conditions into the sterilized packaging unit. Next, the conduit between the location of the sterile connecting step and the entrance to the sterilized packaging unit is permanently sealed by heat sealing, radio frequency sealing, or the like, followed by severing all material upstream of the seal in order to form the finished packaging unit product.

The following specific examples will more precisely illustrate the invention and teach the procedures that are presently preferred for practicing the same.

EXAMPLE I

An autoclavable dispenser molded of polyvinyl chloride and having a multiplicity of sterile connectors depending therefrom was autoclaved in a conventional apparatus with water and steam at a temperature of about 120° C. in order to sterilize a liquid anticoagulant sealed therewithin as well as the interior surfaces of the dispenser and its associated tubing. A blood bag of a structure generally illustrated in the drawings was molded of ethylene vinyl acetate polymer and subjected to gas sterilization with ethylene oxide gas. The blood bag was first preconditioned by partial evacuation, followed by adding steam thereinto and heating to a temperature of about 40° C. after which sterilization exposure was accomplished by adding under pressure a mixture of ethylene oxide and freon at a ratio of 12:88, maintaining the same elevated temperature and a relative humidity of about 50%. Exposure continued for approximately four hours, after which flushing was accomplished by evacuating the thus sterilized blood bag and repressurizing or flushing with air, followed by repeating the evacuation and repressurizing steps in order to remove residual sterilant.

The respective sterile connectors from the gas-sterilized blood bag and from the autoclaved dispenser were secured to each other in opposing relationship, after which the opaque thermoplastic opposing wall members thereof were exposed to infrared radiation provided by two 150-watt lamps having elliptical reflectors. Exposure proceeded for about 15 seconds until the opaque wall portions fused and the aperture was formed. Bacteria trapped on the wall portion was killed by the heating or was entrapped upon rehardening of the opaque wall portions in order to form a sterile flow channel. Then, 63 ml of citrate phosphate dextrose anticoagulant solution was passed into the primary container, the connecting tubing was radio frequency sealed, and the sterile connectors were severed from the completed non-autoclaved blood bag.

While in the foregoing specification certain embodiments and examples of this invention have been described in detail, it will be appreciated that modifications and variations therefrom will be apparent to those skilled in this art. Accordingly, this invention is to be limited only by the scope of the appended claims.

I claim:

1. A method of preparing liquid-containing sterile packages comprising the steps of:
    fabricating a package which has a normally empty fluid chamber and which can be effectively sterilized only by dry-sterilization techniques;
    fabricating a dispensing container which has a normally empty fluid chamber and which can be effectively sterilized by wet-sterilization techniques;
    sterilizing said package by a dry-sterilization technique with its fluid chamber empty;
    introducing a liquid into the fluid chamber of said dispensing container;
    sterilizing by a wet-sterilization technique said dispensing container and the liquid contained within its fluid chamber;
    providing a sterile flow path between the fluid chambers of said wet-sterilized dispensing container and said dry-sterilized package;
    transporting through said sterile flow path a premeasured unit of said sterilized liquid from out of the fluid chamber of said wet-sterilized dispensing container and into the fluid chamber of said dry-sterilized package;
    sealing said sterile flow path; and
    severing said wet-sterilized dispensing container from said now filled, dry-sterilized package.

2. The method of claim 1, wherein said step of providing a sterile flow path includes exposing opaque, thermoplastic material to radiant energy for fusing it into a sterile aperture.

3. The method of claim 1, wherein said step of providing a sterile flow path includes making a connection between said sterilized package and said sterilized dispensing container, and opening the connection under sterile conditions to form said sterile flow path.

4. A method for preparing liquid-containing sterile packages from non-autoclavable material, comprising the steps of:
    selecting a non-autoclavable material that is unsuitable for withstanding autoclave conditions and that is especially suitable for prolonged storage of body fluids;
    forming from said non-autoclavable material a package having an initially empty fluid chamber;
    sterilizing by a dry-sterilization technique said non-autoclavable package with its fluid chamber empty;
    selecting an autoclavable substance;
    forming from said autoclavable substance a dispensing container having an initially empty fluid chamber;
    introducing a fluid into the fluid chamber of the dispensing container;
    sterilizing by a wet-sterilization technique said autoclavable dispensing container and the liquid contained within its fluid chamber;
    providing a sterile flow path between said liquid filled wet-sterilized dispensing container and said empty, dry-sterilized package;
    introducing through said sterile flow path a premeasured unit of said sterilized liquid from out of the fluid chamber of said wet-sterilized dispensing container and into the fluid chamber of said dry-sterilized package;
    sealing said sterile flow path; and
    severing said dispensing container from said now filled dry-sterilized package.

5. The method of claim 4, wherein said step of providing a sterile flow path includes exposing opaque, thermoplastic material to radiant energy for fusing it into a sterile aperture.

6. The method of claim 4, wherein said step of providing a sterile flow path includes connecting in a sterile manner said sterilized dispensing container with said sterilized package.

7. The method of claim 4, wherein said step of sterilizing said autoclavable dispensing container is at a temperature of at least about 114° C.

8. The method of claim 4, wherein said step of sterilizing said autoclavable dispensing container is an autoclave step at a temperature of at least about 120° C.

9. The method of claim 4, wherein said step of dry-sterilizing said non-autoclavable package comprises radiation sterilization at between about 1 megarad and 5 megarads.

10. The method of claim 4, wherein said step of dry-sterilizing said non-autoclavable package comprises gas sterilization.

11. The method of claim 4, wherein said step of dry-sterilizing said non-autoclavable package includes treating with ethylene oxide gas at a temperature between about 20° and about 70° C.

* * * * *